US006809315B2

(12) United States Patent
Ellson et al.

(10) Patent No.: US 6,809,315 B2
(45) Date of Patent: *Oct. 26, 2004

(54) METHOD AND SYSTEM USING ACOUSTIC EJECTION FOR PREPARING AND ANALYZING A CELLULAR SAMPLE SURFACE

(75) Inventors: Richard N. Ellson, Palo Alto, CA (US); Mitchell W. Mutz, Palo Alto, CA (US); Richard Michael Caprioli, Brentwood, TN (US)

(73) Assignee: Picoliter Inc., Mountain View, CA (US)

( * ) Notice: Subject to any disclaimer, the term of this patent is extended or adjusted under 35 U.S.C. 154(b) by 125 days.

This patent is subject to a terminal disclaimer.

(21) Appl. No.: 10/087,372

(22) Filed: Mar. 1, 2002

(65) Prior Publication Data

US 2002/0171037 A1 Nov. 21, 2002

Related U.S. Application Data

(63) Continuation-in-part of application No. 10/066,546, filed on Jan. 30, 2002, which is a continuation-in-part of application No. 09/784,705, filed on Feb. 14, 2001, now Pat. No. 6,603,118.

(51) Int. Cl.[7] .......................... H01J 49/04; G01N 1/10; G01N 35/10
(52) U.S. Cl. ...................... 250/288; 436/180; 422/100; 422/63; 435/30; 73/864; 73/864.81
(58) Field of Search ...................... 250/288; 436/180; 422/100, 63; 435/30; 73/864

(56) References Cited

U.S. PATENT DOCUMENTS

| 4,308,547 A | 12/1981 | Lovelady et al. |
| 4,751,529 A | 6/1988 | Elrod et al. |
| 5,306,412 A | 4/1994 | Whitehouse et al. |
| 5,520,715 A | 5/1996 | Oeftering |
| 5,722,479 A | 3/1998 | Oeftering |

(List continued on next page.)

FOREIGN PATENT DOCUMENTS

EP 0434931 A2 7/1991

OTHER PUBLICATIONS

U.S. patent application Ser. No. 09/669,267, Ellson, filed Sep. 25, 2000.
U.S. patent application Ser. No. 09/669,996, Ellson et al., filed Sep. 25, 2000.
U.S. patent application Ser. No. 09/669,997, Mutz et al., Sep. 25, 2000.
U.S. patent application Ser. No. 09/999,166, Mutz et al., Nov. 29, 2001.

(List continued on next page.)

Primary Examiner—Jack Berman
(74) Attorney, Agent, or Firm—Louis L. Wu; Reed & Eberle LLP (57) ABSTRACT

The invention relates to a method and system for acoustically depositing a fluid on a surface of a cell sample. A reservoir containing a fluid is provided, and the cell sample surface is positioned in droplet-receiving relationship to the reservoir. Once the reservoir and the cell sample surface are appropriately positioned, focused acoustic energy is applied to eject a droplet of the fluid from the reservoir. As a result, the droplet is deposited on the sample surface at a designated site. Optionally, the fluid may be an analysis-enhancing fluid that contains a label moiety or a mass-spectrometry matrix material. When an analysis-enhancing fluid is used, the sample is typically subjected to conditions effective to allow the analysis-enhancing fluid to interact with the sample surface so as to render the sample surface suitable for analysis. Then, the sample may be analyzed at the designated site.

70 Claims, 2 Drawing Sheets

U.S. PATENT DOCUMENTS

| | | | | |
|---|---|---|---|---|
| 5,798,779 | A | | 8/1998 | Nakayasu et al. |
| 5,808,300 | A | * | 9/1998 | Caprioli ..................... 250/288 |
| 5,808,636 | A | | 9/1998 | Stearns |
| 5,877,580 | A | | 3/1999 | Swierkowski |
| 6,322,970 | B1 | | 11/2001 | Little et al. |
| 6,558,902 | B1 | | 5/2003 | Hillenkamp |
| 2002/0037579 | A1 | | 3/2002 | Ellison et al. |
| 2002/0064808 | A1 | | 5/2002 | Mutz et al. |
| 2002/0064809 | A1 | | 5/2002 | Mutz et al. |
| 2002/0090720 | A1 | | 7/2002 | Mutz et al. |
| 2002/0094582 | A1 | * | 7/2002 | Williams et al. ............ 436/180 |
| 2002/0061258 | A1 | | 5/2003 | Mutz et al. |

OTHER PUBLICATIONS

Amemiya et al. (1997), *Proceedings of the 1997 IS&T's NIP 13: International Conference on Digital Printing Technologies*, pp. 698–702.

IUPAC–IUB Commission on Biochemical Nomenclature (CBN) (1970), "Abbreviations and Symbols for Nucleic Acids, Polynucleotides and Their Constituents," *Biochemistry* 9(20):4022–4025.

Karas et al. (1988), "Laser Desorption Ionization of Proteins with Molecular Masses Exceeding 10,000 Daltons," *Anal. Chem.* 60:2299–2301.

Steel et al. (2000), "The Flow–Thru Chip™: A Three–Dimensional Biochip Platform," *Microarray Biochip Technology*, Chapter 5, pp. 87–117, BioTechniques Books, Natick, MA.

Stoeckli et al. (2001), "Imaging Mass Spectrometry: A New Technology for the Analysis of Protein Expression in Mammalian Tissues," *Nature Medicine* 7(4):493–496.

* cited by examiner

METHOD AND SYSTEM USING ACOUSTIC EJECTION FOR PREPARING AND ANALYZING A CELLULAR SAMPLE SURFACE

CROSS-REFERENCE TO RELATED APPLICATIONS

This is a continuation-in-part of U.S. patent application Ser. No. 10/066,546, filed Jan. 30, 2002, which is a continuation-in-part of U.S. patent application Ser. No. 09/784,705, filed Feb. 14, 2001, now U.S. Pat. No. 6,603,118 the disclosures of which are incorporated by reference herein.

TECHNICAL FIELD

This invention relates generally to methods and devices for preparing and optionally analyzing a cellular sample surface. More particularly, the invention relates to the use of nozzleless acoustic ejection to deposit droplets from a reservoir containing an analysis-enhancing fluid to designated sites on a cellular sample surface. The invention is particularly useful in enhancing the compositional analysis of the sample at the designated sites and in the mass spectrometric imaging of tissue surfaces.

BACKGROUND

Cellular assays are carried out to provide critical information for the understanding of complex cell functions. One commonly employed technique used in cellular assays involves the immobilization of sample cells on a substrate surface and the controlled exposure of the cells to one or more fluids. Particularly when the sample is small, such assays may require the precise and accurate handling of small volumes of fluid.

A number of techniques have been developed in order to meet the need for precise and accurate handling of small volumes of fluids, but most suffer from one drawback or another. For example, capillaries having a small interior channel (e.g., Eppendorf-type capillaries) are often used to transfer fluids from a pool of fluid. Their tips are submerged in the pool in order to draw fluid therefrom. In order to provide sufficient mechanical strength for handling, however, such capillaries must have a large wall thickness as compared to the interior channel diameter. Thus, the physical dimensions of such capillaries limit their fluid-handling capability. In addition, since any wetting of the exterior capillary surface results in fluid waste, the high wall thickness to channel diameter ratio exacerbates fluid waste. Also, the pool has a minimum required volume driven not by the fluid introduced into the capillary but, rather, by the need to immerse the large exterior dimension of the capillary. As a result, the fluid volume required for capillary submersion may be more than an order of magnitude larger than the fluid volume transferred into the capillary.

Mass spectrometry is a well-established analytical technique in which sample molecules are ionized and the resulting ions are sorted by mass-to-charge ratio. Mass spectrometry has been employed for samples that have been prepared as an array of features on a substrate surface. Surface-based mass spectrometry has been used, for example, to analyze single nucleotide polymorphisms in microarray formats. See, e.g., U.S. Pat. No. 6,322,970 to Little et al.

Matrix-Assisted Laser Desorption Ionization (MALDI) is an ionization technique often used for mass spectrometric analysis of large and/or labile biomolecules, such as nucleotidic and peptidic oligomers, polymers, and dendrimers, as well as for analysis of non-biomolecular compounds, such as fullerenes. MALDI is considered a "soft" ionizing technique in which both positive and negative ions are produced. The technique involves depositing a small volume of sample fluid containing an analyte on a substrate comprised of a photon-absorbing matrix material selected to enhanced desorption performance. See Karas et al. (1988), "Laser Desorption Ionization of Proteins with Molecular Masses Exceeding 10,000 Daltons," *Anal. Chem.*, 60:2299–2301. The matrix material is usually a crystalline organic acid that absorbs electromagnetic radiation near the wavelength of the laser. When co-crystallized with analyte, the matrix material assists in the ionization and desorption of analyte moieties. The sample fluid typically contains a solvent and the analyte. Once the solvent has been evaporated from the substrate, the analyte remains on the substrate at the location where the sample fluid is deposited. Photons from a laser strike the substrate at the location of the analyte and, as a result, ions and neutral molecules are desorbed from the substrate. MALDI techniques are particularly useful in providing a means for efficiently analyzing a large number of samples. In addition, MALDI is especially useful in the analysis of minute amounts of sample that are provided over a small area of a substrate surface.

Surface Enhanced Laser Desorption Ionization (SELDI) is another example of a surface-based ionization technique that allows for high-throughput mass spectrometry. SELDI uses affinity capture reagents such as antibodies to collect samples from a complex mixture, which allows in situ purification of the analyte followed by conventional MALDI analysis. Typically, SELDI is used to analyze complex mixtures of proteins and other biomolecules. SELDI employs a chemically reactive surface such as a "protein chip" to interact with analytes, e.g., proteins, in solution. Such surfaces selectively interact with analytes and immobilize them thereon. Thus, analytes can be partially purified on the chip and then quickly analyzed in the mass spectrometer. By providing different reactive moieties at different sites on a substrate surface, throughput may be increased.

Recently, mass spectrometry techniques involving laser desorption have been adapted for cellular analysis. U.S. Pat. No. 5,808,300 to Caprioli, for example, describes a method for imaging biological samples with MALDI mass spectrometry. This method allows users to measure the distribution of an element or small molecule in biological specimens, including tissue slices and individual cells. In particular, the method can be used for the specific analysis of peptides in whole cells, e.g., by obtaining signals for peptides and proteins directly from tissues and blots of tissues. In addition, the method has been used to desorb relatively large proteins from tissues and blots of tissues in the molecular weight range beyond about 80 kilodaltons. From such samples, hundreds of peptide and protein peaks can be recorded in the mass spectrum produced from a single laser-ablated site on the sample. When a laser ablates the surface of the sample at multiple sites and the mass spectrum from each site is saved separately, a data array is produced which contains the relative intensity of any mass at each site. An image of the sample surface can then be constructed for any given molecular weight, effectively representing a compositional map of the sample surface.

One important issue to successful MALDI profiling and imaging as described above is the application of a controlled or uniform coating of a mass-spectrometry matrix material to the tissue surface, either as a series of features or as a continuous coating. The ability to closely compare relative abundances of a given protein between two tissues is dependent on the application of matrix in exactly the same way. Most current small-volume dispensing techniques are not reliable for matrix material application as needed, due to limitations in volume or in accuracy of placement.

A number of patents have described the use of acoustic energy in printing. For example, U.S. Pat. No. 4,308,547 to Lovelady et al. describes a liquid drop emitter that utilizes acoustic principles in ejecting droplets from a body of liquid ink onto a moving document to form characters or bar codes thereon. As described in a number of U.S. patent applications, acoustic ejection provides for highly accurate deposition of minute volumes of fluids on a surface, wherein droplet volume—and thus "spot" size on the substrate surface—can be carefully controlled, and droplets can be precisely directed to particular sites on a substrate surface. See, e.g., U.S. Ser. Nos. 09/669,996 and 09/964,212 for "Acoustic Ejection of Fluids from a Plurality of Reservoirs", inventors Ellson, Foote and Mutz, filed Sep. 25, 2000 and Sep. 25, 2001, respectively, and assigned to Picoliter Inc. (Mountain View, Calif.). In other words, nozzleless fluid delivery provides high fluid-delivery efficiency through accurate and precise droplet placement. Nozzleless fluid ejection also provides a high level of control over ejected droplet size.

While nozzleless fluid ejection has generally been appreciated for ink printing applications, acoustic deposition is a generally unknown technique in the field of cellular analysis. Recently, focused acoustic energy has been used to manipulate cells and engage in cell sorting. See U.S. Ser. Nos. 09/727,391 and 09/999,166, filed Nov. 29, 2001 and Nov. 29, 2001, respectively for "Focused Acoustic Energy for Ejection Cells from a Fluid," inventors, Mutz and Ellson, assigned to Picoliter Inc. (Mountain View, Calif.), and U.S. Ser. Nos. 10/040,926 and 10/033,739, filed Dec. 28, 2001 and Dec. 27, 2001, respectively, for "Focused Acoustic Ejection Cell Sorting System and Method," inventors Mutz, Ellson, and Lee, assigned to Picoliter Inc. (Mountain View Calif.). Thus, there exist opportunities to improve cellular assay and analysis techniques through the use of acoustic ejection.

SUMMARY OF THE INVENTION

In a first embodiment, the invention relates to a method for acoustically depositing droplets of a fluid on a surface of a cell sample. The method involves first providing a reservoir containing a fluid and positioning the cell sample surface in droplet-receiving relationship to the reservoir. Once the reservoir and the cell sample surface are appropriately positioned, focused acoustic energy is applied to eject a droplet of the fluid from the reservoir. As a result, the droplet is deposited on the sample surface at a designated site.

In another embodiment, a system is provided for acoustically depositing droplets of a fluid on a surface of a cellular sample. The system includes a reservoir containing a fluid, an acoustic ejector, an acoustic ejector positioning means, a cellular sample having a surface, and a sample positioning means. The acoustic ejector includes an acoustic radiation generator for generating acoustic radiation and a focusing means for focusing the acoustic radiation generated. The ejector positioning means is adapted for positioning the acoustic ejector in acoustic coupling relationship to the reservoir. The sample positioning means is adapted for positioning the cellular sample surface such that at least one designated site thereon is in droplet-receiving relationship to the reservoir.

For any embodiment of the invention, the cellular sample may comprise cells from a number of sources. For example, the cells may be extracted from any living or nonliving organism, or they may be taken from a cell culture. In some instances, the cellular sample is a tissue taken from a mammal. The surface of the cellular sample may be compositionally uniform or nonuniform.

Similarly, the fluid used in the invention may vary. For example, the fluid may be or include an analysis-enhancing fluid. In some instances, the analysis-enhancing fluid may contain a detectable label that may be fluorescent, magnetic, or radioactive. Other types of detectable labels may be employed as well. For example, the label moiety may be enzymatic in nature. Furthermore, the fluid may be selected to preferentially interact with specific moieties on the sample surface. Such fluids may contain, for example, enzymes, whole cells, cell extracts, peptides, or nucleotides.

When an analysis-enhancing fluid is used, the sample is typically subjected to conditions effective to allow the analysis-enhancing fluid to interact with the sample surface so as to render the sample surface suitable for analysis. Then, the sample may be analyzed at the designated site. Analysis may range from inspection, in order to determine the extent of any interaction between the analysis-enhancing fluid and the sample surface, to mass spectrometric analysis. MALDI and/or SELDI type techniques may be employed in which energy applied to the designated site effects the release of sample molecules from the sample surface for analysis.

Optionally, a plurality of droplets may be ejected from one or more reservoirs and deposited on the sample surface. In some instances, the droplets are deposited on the sample surface at a single designated site. In other instances, the droplets are deposited on the sample surface at different designated sites. As a result, an array of droplets may be formed on the sample surface so that when the composition of the sample is analyzed at each designated site, a compositional map of the cellular sample surface may be produced.

Thus, another embodiment of the invention relates to a method for analyzing a surface of a cellular sample. The method involves: (a) providing a reservoir containing an analysis-enhancing fluid; (b) positioning the cellular sample surface such that a designated site on the cellular sample surface is in droplet-receiving relationship to the fluid containing reservoir, wherein the designated site is one of a plurality of designated sites within an array of such sites; (c) applying focused acoustic energy in a manner effective to eject a droplet of the fluid from the reservoir such that the droplet is deposited on the sample surface at the designated site; (d) repeating step (b) and (c) with each different designated site so that at least one droplet is deposited at each designated site; (e) applying energy to each of the designated sites to effect release of sample molecules therefrom; and (f) analyzing the released sample molecules. Optionally, analysis of the released sample molecules involves producing a compositional map of the cellular sample surface from the results of mass spectrometric analysis.

Furthermore, the invention provides a system for acoustically depositing a fluid on a surface of a cellular sample. The system comprises: a reservoir containing an analyte-enhancing fluid; an acoustic ejector comprising an acoustic radiation generator for generating acoustic radiation and a focusing means for focusing the acoustic radiation that is generated; an acoustic ejector positioning means for positioning the acoustic ejector in acoustic coupling relationship to the reservoir; a cellular sample having a surface; a sample positioning means for positioning a cellular sample surface such that a plurality of different designated sites within an array of such sites on the cellular sample surface are successively placed in droplet-receiving relationship to the reservoir; an energy-applying means for applying energy to the designated sites to effect release and ionization of sample molecules therefrom; and an analyzing means for analyzing the sample molecules from the designated sites. Optionally, the energy applying means comprises a photon bombarding means such as a laser, for bombarding the designated site with photons; and the analyzing means comprises a mass spectrometer.

BRIEF DESCRIPTION OF THE DRAWINGS

The invention is described in detail below with reference to the following drawings, wherein like reference numerals indicate a corresponding structure throughout the several views. The figures illustrate an embodiment of the inventive method wherein a tissue sample is analyzed through laser desorption-based mass spectrometry.

DETAILED DESCRIPTION OF THE INVENTION

Definitions and Overview:

Before describing the present invention in detail, it is to be understood that this invention is not limited to specific fluids, biomolecules, or device structures, as such may vary. It is also to be understood that the terminology used herein is for the purpose of describing particular embodiments only, and is not intended to be limiting.

It must be noted that, as used in this specification and the appended claims, the singular forms "a," "an," and "the" include both singular and plural referents unless the context clearly dictates otherwise. Thus, for example, reference to "a reservoir" includes a plurality of reservoirs as well as a single reservoir, reference to "a fluid" includes a combination or mixture of fluids as well as a single fluid, reference to "a biomolecule" includes a combination of biomolecules as well as single biomolecule, and the like.

In describing and claiming the present invention, the following terminology will be used in accordance with the definitions set out below.

The terms "acoustic coupling" and "acoustically coupled" as used herein refer to a state wherein an object is placed in direct or indirect contact with another object so as to allow acoustic radiation to be transferred between the objects without substantial loss of acoustic energy. When two items are indirectly acoustically coupled, an "acoustic coupling medium" is needed to provide an intermediary through which acoustic radiation may be transmitted. Thus, an ejector may be acoustically coupled to a fluid, e.g., by immersing the ejector in the fluid or by interposing an acoustic coupling medium between the ejector and the fluid to transfer acoustic radiation generated by the ejector through the acoustic coupling medium and into the fluid.

The term "adsorb" as used herein refers to the noncovalent retention of a molecule or a cell by a surface. That is, adsorption occurs as a result of noncovalent interaction between a surface and adsorbing moieties present on the molecule. Adsorption may occur through hydrogen bonding, van der Waal's forces, polar attraction, or electrostatic forces (i.e., through ionic bonding). Examples of adsorbing moieties include, but are not limited to, amine groups, carboxylic acid moieties, hydroxyl groups, nitroso groups, sulfones, and the like.

The term "adsorb" is often used in the context of substrate or sample surfaces. The substrate or sample surface commonly may be functionalized with adsorbent moieties to interact in a certain manner, as when the surface is functionalized with amino groups to render it positively charged in a pH-neutral aqueous environment. Likewise, adsorbate moieties may be added in some cases to effect adsorption, as when a basic protein is fused with an acidic peptide sequence to render adsorbate moieties that can interact electrostatically with a positively charged adsorbent moiety.

The term "array" as used herein refers to a two-dimensional arrangement of features, such as an arrangement of reservoirs (e.g., wells in a well plate) or an arrangement of fluid droplets or molecular moieties on a substrate surface (as in an oligonucleotide or peptide array). Arrays are generally comprised of features regularly ordered in, for example, a rectilinear grid, parallel stripes, spirals, and the like, but non-ordered arrays may be advantageously used as well. An array differs from a pattern in that patterns do not necessarily contain regular and ordered features. In addition, arrays and patterns formed by the deposition of ejected droplets on a surface, as provided herein, are usually substantially invisible to the unaided human eye. Arrays typically, but do not necessarily, comprise at least about 4 to about 10,000,000 features, generally in the range of about 4 to about 1,000,000 features.

The term "attached," as in, for example, a substrate surface having a molecular moiety "attached" thereto, includes covalent binding, adsorption, and physical immobilization. The terms "binding" and "bound" as used herein are identical in meaning to the term "attached."

The terms "biomolecule" and "biological molecule" are used interchangeably herein to refer to any organic molecule—whether naturally occurring, recombinantly produced, or chemically synthesized in whole or in part—that is, was, or can be a part of a living organism. The terms encompass, for example, nucleotides, amino acids, and monosaccharides, as well as oligomeric and polymeric species such as oligonucleotides and polynucleotides, peptidic molecules such as oligopeptides, polypeptides and proteins, polysaccharides such as disaccharides, oligosaccharides, mucopolysaccharides, and peptidoglycans (peptidopolysaccharides), and the like. The term also encompasses ribosomes, enzyme cofactors, pharmacologically active agents, and the like.

The terms "cell" and "cellular" are used herein with their ordinary biological meaning and refer to the smallest structural unit of an organism, living or not, that is capable of independent functioning, and includes of one or more nuclei, cytoplasm, and various organelles, all surrounded by a semipermeable membrane. The term "cellular sample" as used herein refers to a sample that typically contains a plurality of cells. The cells may be of the same type or different types. When the cellular sample contains a single cell, the cell is a large, e.g., a fertilized or unfertilized cell. Any number of processing techniques may be used to prepare a cellular sample. For example, the cells may be cultured or extracted from living or dead organisms. In addition, the cellular samples may be prepared for microscopy, e.g., through smears, squashes, mounts, and sections.

The term "moiety" as used herein refers to any particular composition of matter, e.g., a molecular fragment, an intact molecule, or a mixture of materials.

It will be appreciated that, as used herein, the terms "nucleoside" and "nucleotide" refer to nucleosides and nucleotides containing not only the conventional purine and pyrimidine bases, i.e., adenine (A), thymine (T), cytosine (C), guanine (G), and uracil (U), but also protected forms thereof, e.g., wherein the base is protected with a protecting group such as acetyl, difluoroacetyl, trifluoroacetyl, isobutyryl, or benzoyl, and purine and pyrimidine analogs. Suitable analogs will be known to those skilled in the art and are described in the pertinent texts and literature. Common analogs include, but are not limited to, 1-methyladenine, 2-methyladenine, $N^6$-methyladenine, $N^6$-isopentyladenine, 2-methylthio-$N^6$-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine, and 2,6-diaminopurine. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

As used herein, the term "oligonucleotide" is generic to polydeoxynucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones (for example, PNAs), provided that the polymers contain nucleobases in a configuration that allows for base pairing and base stacking, such as are found in DNA and RNA. Thus, these terms include known types of oligonucleotide modifications, for example, substitution of one or more of the naturally occurring nucleotides with an analog; internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters); those containing pendant moieties such as, for example, proteins (including nucleases, toxins, antibodies, signal peptides, poly-L-lysine, etc.), those with intercalators (e.g., acridine, psoralen, etc.), and those containing chelators (e.g., metals, radioactive metals, boron, oxidative metals, etc.). There is no intended distinction in polymer length between the terms "polynucleotide" and "oligonucleotide," and these terms will be used interchangeably. These terms refer only to the primary structure of the molecule. As used herein, the symbols for nucleotides and polynucleotides are according to the IUPAC-IUB Commission of Biochemical Nomenclature recommendations (*Biochemistry* 9:4022, 1970).

The terms "peptide," "peptidyl," and "peptidic" as used throughout the specification and claims are intended to include any structure comprised of two or more amino acids. For the most part, the peptides in the present arrays comprise about 5 to 10,000 amino acids, preferably about 5 to 1000 amino acids. The amino acids forming all or a part of a peptide may be any of the twenty conventional, naturally occurring amino acids, i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y). Any of the amino acids in the peptidic molecules that form the present arrays may be replaced by a non-conventional amino acid. In general, conservative replacements are preferred. Conservative replacements substitute the original amino acid with a non-conventional amino acid that resembles the original in one or more of its, characteristic properties (e.g., charge, hydrophobicity, stearic bulk; for example, one may replace Val with Nval). The term "non-conventional amino acid" refers to amino acids other than conventional amino acids, and includes, for example, isomers and modifications of the conventional amino acids (e.g., D-amino acids), non-protein amino acids, post-translationally modified amino acids, enzymatically modified amino acids, constructs or structures designed to mimic amino acids (e.g., α,α-disubstituted amino acids, N-alkyl amino acids, lactic acid, β-alanine, naphthylalanine, 3-pyridylalanine, 4-hydroxyproline, O-phosphoserine, N-acetylserine, N-formylmethionine, 3-methylhistidine, 5-hydroxylysine, and norleucine), and peptides having the naturally occurring amide —CONH— linkage replaced at one or more sites within the peptide backbone with a non-conventional linkage such as N-substituted amide, ester, thioamide, retropeptide (—NHCO—), retrothioamide (—NHCS—), sulfonamido (—SO$_2$NH—), and/or peptoid (N-substituted glycine) linkages. Accordingly, the peptidic molecules of the array include pseudopeptides and peptidomimetics. The peptides of this invention can be (a) naturally occurring, (b) produced by chemical synthesis, (c) produced by recombinant DNA technology, (d) produced by biochemical or enzymatic fragmentation of larger molecules, (e) produced by methods resulting from a combination of methods (a) through (d) listed above, or (f) produced by any other means for producing peptides.

The term "fluid" as used herein refers to matter that is nonsolid or at least partially gaseous and/or liquid. A fluid may contain a solid that is minimally, partially, or fully solvated, dispersed, or suspended. Examples of fluids include, without limitation, aqueous liquids (including water per se and salt water) and nonaqueous liquids such as organic solvents and the like. As used herein, the term "fluid" is not synonymous with the term "ink," in that ink must contain a colorant and may not be gaseous. However, the term "fluid" is intended to encompass fluid inks.

The terms "focusing means" and "acoustic focusing means" refer to a means for causing acoustic waves to converge at a focal point by either a device separate from the acoustic energy source that acts like an optical lens, or by the spatial arrangement of acoustic energy sources to effect convergence of acoustic energy at a focal point by constructive and destructive interference. A focusing means may be as simple as a solid member having a curved surface, or it may include complex structures such as those found in Fresnel lenses, which employ diffraction in order to direct acoustic radiation. Suitable focusing means also include phased array methods as known in the art and as described, for example, in U.S. Pat. No. 5,798,779 to Nakayasu et al. and Amemiya et al. (1997) *Proceedings of the 1997 IS&T NIP13 International Conference on Digital Printing Technologies*, pp. 698–702.

The term "ion" is used in its conventional sense to refer to a charged atom or molecule, i.e., an atom or molecule that contains an unequal number of protons and electrons. Positive ions contain more protons than electrons, and negative ions contain more electrons than protons. Ordinarily, an ion of the present invention is singly charged, but may, in certain instances, have a multiple charge.

The term "near," as used herein refers to the distance from the focal point of the focused acoustic radiation to the surface of the fluid from which a droplet is to be ejected, indicates that the distance should be such that the focused acoustic radiation directed into the fluid results in droplet ejection from the fluid surface; and that one of ordinary skill in the art will be able to select an appropriate distance for any given fluid using straightforward and routine experimentation. Generally, however, a suitable distance between the focal point of the acoustic radiation and the fluid surface is in the range of about 1 to about 15 times the wavelength of the speed of sound in the fluid, more typically in the range of about 1 to about 10 times that wavelength, preferably in the range of about 1 to about 5 times that wavelength.

"Optional" or "optionally" means that the subsequently described circumstance may or may not occur, so that the description includes instances when the circumstance occurs and instances when it does not.

The term "reservoir" as used herein refers to a receptacle or chamber for containing a fluid. Thus, a fluid in a reservoir necessarily has a free surface, i.e., a surface that allows a droplet to be ejected therefrom. A reservoir may also be a locus on a substrate surface within which a fluid is constrained or held. In some instances, a reservoir may represent a portion, e.g., a fluid-transporting feature of a microfluidic device.

The term "substantially" as in, for example, the phrase "substantially identical reservoirs" refers to reservoirs that do not deviate in acoustic properties. For example acoustic attenuation of "substantially identical reservoirs" by more than 10%, preferably not more than 5%, more preferably not more than 1%, and most preferably at most 0.1% from each other. Other uses of the term "substantially" involve an analogous definition.

The term "substrate" as used herein refers to any material having a surface onto which a cellular sample may be placed and optionally immobilized. The substrate may be constructed in any of a number of forms, for example, such as wafers, slides, well plates, and membranes. In addition, the substrate may be porous or nonporous as may be required for deposition of a particular fluid. Suitable substrate materials include, but are not limited to, supports that are typically used for solid phase chemical synthesis, e.g., polymeric materials (e.g., polystyrene, polyvinyl acetate, polyvinyl chloride, polyvinyl pyrrolidone, polyacrylonitrile, polyacrylamide, polymethyl methacrylate, polytetrafluoroethylene, polyethylene, polypropylene, polyvinylidene fluoride, polycarbonate, divinylbenzene styrene-based polymers), agarose (e.g., Sepharose®), dextran (e.g., Sephadex®), cellulosic polymers and other polysaccharides, silica and silica-based materials, glass (particularly controlled pore glass, or "CPG") and functionalized glasses, ceramics, and such substrates treated with surface coatings, e.g., with microporous polymers (particularly cellulosic polymers such as nitrocellulose), microporous metallic compounds (particularly microporous aluminum), antibody-binding proteins (available from Pierce Chemical Co., Rockford Ill.), bisphenol A polycarbonate, or the like.

Substrates may be porous, and include, as alluded to above: uncoated porous glass slides, including CPG slides; porous glass slides coated with a polymeric coating, e.g., an aminosilane or poly-L-lysine coating, thus having a porous polymeric surface; and nonporous glass slides coated with a porous coating. The porous coating may be a porous polymer coating, such as may be comprised of a cellulosic polymer (e.g., nitrocellulose) or polyacrylamide, or a porous metallic coating (for example, comprised of microporous aluminum). Examples of commercially available substrates having porous surfaces include the Fluorescent Array Surface Technology (FAST™) slides available from Schleicher & Schuell, Inc. (Keene, N.H.), which are coated with a 10–30 $\mu$m thick porous, fluid-permeable nitrocellulose layer that substantially increases the available binding area per unit area of surface. Other commercially available porous substrates include the CREATIVECHIP® permeable slides currently available from Eppendorf AG (Hamburg, Germany) and substrates having "three-dimensional" geometry by virtue of an ordered, highly porous structure that enables reagents to flow into and penetrate through the pores and channels of the entire structure. Such substrates are available from Gene Logic, Inc., under the tradename "Flow-Thru Chip," and are described by Steel et al. in Chapter 5 of *Microarray Biochip Technology* (BioTechniques Books, Natick, Mass., 2000).

The term "porous," as in a "porous substrate" or a "substrate having a porous surface," refers to a substrate or surface, respectively, having a porosity (void percentage) in the range of about 1% to about 99%, preferably about 5% to about 99%, more preferably in the range of about 15% to about 95%, and an average pore size of about 100 Å to about 1 mm, typically about 500 Å to about 0.5 mm.

The term "impermeable" is used in the conventional sense to mean not permitting water or other fluids to pass through. The term "permeable" as used herein means not "impermeable." Thus, a "permeable substrate" and a "substrate having a permeable surface" refer to a substrate or surface, respectively, which can be permeated with water or other fluid.

While the foregoing support materials are representative of conventionally used substrates, it is to be understood that a substrate may, in fact, comprise any biological, nonbiological, organic, and/or inorganic material, and may be in any of a variety of physical forms, e.g., particles, strands, precipitates, gels, sheets, tubing, spheres, containers, capillaries, pads, slices, films, plates, and the like, and may further have any desired shape, such as a disc, square, sphere, circle, etc. The substrate surface may or may not be flat, e.g., the surface may contain raised or depressed regions. A substrate may additionally contain or be derivatized to contain reactive functionalities that covalently link a compound to the substrate surface. These are widely known and include, for example, silicon dioxide supports containing reactive Si—OH groups, polyacrylamide supports, polystyrene supports, polyethylene glycol supports, and the like.

The term "surface modification" as used herein refers to the chemical and/or physical alteration of a surface by an additive or subtractive process to change one or more chemical and/or physical properties of a substrate surface, or a selected site or region of a substrate surface. For example, surface modification may involve (1) changing the wetting properties of a surface, (2) functionalizing a surface, i.e., providing, modifying, or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

The term "tissue" as used herein refers to an aggregation of morphologically similar cells and associated intercellular matter acting together to perform one or more specific functions in a multicellular organism, e.g., a plant or an animal. When the tissue is from an animal, for example, the tissue may be muscle, nerve, epidermal, or connective.

In general, the invention relates to methods and devices that effect the acoustic deposition of a fluid on a surface of a cellular sample. In essence, focused acoustic energy is applied to a reservoir holding a fluid in a manner effective to eject a droplet of the fluid from the reservoir. When the sample surface is positioned in droplet-receiving relationship to the fluid-containing reservoir, the droplet is deposited on the sample surface at a designated site. Such fluid deposition is useful whenever the precise placement of a fluid on a cellular sample surface is required. For example, the fluid may serve to chemically react with the sample, to preserve the sample, to mark or label the sample, or to prepare the sample for analysis. Typical analytical techniques that benefit from the invention include, for example, mass spectrometry and microscopy.

The invention typically employs a device that includes a reservoir adapted to contain a fluid, an acoustic ejector, an acoustic ejector positioning means, and a sample positioning means. The acoustic ejector comprises an acoustic radiation generator for generating acoustic radiation and a focusing means for focusing the acoustic radiation that is generated. The ejector positioning means is adapted for positioning the acoustic ejector in acoustic coupling relationship to the reservoir. The sample positioning means is adapted for positioning a cellular sample surface, such that at least one designated site thereon is in droplet-receiving relationship to the reservoir.

The cellular sample may comprise nearly any type of cell in the present invention. For example, either or both eukaryotic cells and prokaryotic cells may be used. In some instances, cells extracted are obtained from a mammal. Suitable cell types include, for example, blood cells, stem cells, endothelial cells, epithelial cells, bone cells, liver cells, smooth muscle cells, striated muscle cells, cardiac muscle cells, gastrointestinal cells, nerve cells, and cancer cells. Such cells may be taken as a tissue sample. Alternatively, the cellular sample may comprise cells originating from a cultured cell line or other cultured cells.

The cellular sample may be employed in any of a number of forms. The cellular sample can be compositionally nonuniform. Typically, the cellular sample exhibits a substantially planar surface for ease in array formation when a plurality of droplets is deposited on designated site, as discussed below. In addition, cells are typically immobilized on a substrate surface. Thus, a substrate surface may be selected for facile immobilization of cells. Such surfaces include, for example, a collagen-derivatized surface, dextran, polyacrylamide, nylon, polystyrene, and combinations thereof. In some instances, the surfaces are inherently cytophilic. In other instances, a cytophilic substrate surface is provided as a result of surface modification.

Cells may be immobilized on a substrate surface using conventional techniques known to those skilled in the art. For example, the cells may be immobilized on cytophilic substrate surface simply by contacting the surface with the cells. In some instances, a centrifuge may be used to produce a force sufficient to immobilize cells in a fluid on a substrate surface. In other instances, cytometers known in the art may be used. In still other instances, acoustic ejection, as described in U.S. Ser. Nos. 09/727,391, 09/751,666, 09/999, 166, 10/033,739, and 10/040,926, may be carried out to place cells on a substrate surface. In addition or in the alternative, the substrate surface may be coated with a layer of a cell-adhering substance, such as collagen, alginate, agar, or other material, to immobilize the cells. When immobilization of cells in a contiguous layer is desired, the cell-adhering substance may be contiguously coated on the target region. When it is desirable to provide an immobilized array of cells, however, the cell-adhering substance may be present as an array of features on a substrate surface. That is, an array of locations on a substrate surface may be coated with an appropriate material to form an array (e.g., patterns such as lanes, checkerboards, spots, or others) so that cells may be spatially arranged at specific locations on the solid surface.

When the cellular sample is a tissue sample, any of the above immobilization methods may be used. In addition, immobilization of tissue samples may be accomplished by first freezing a relatively large section of tissue. Thereafter, a slicing means such as a knife, microtome, or similar sectioning device is used to slice the frozen tissue into sections. Next, a single section of the tissue is placed onto the substrate (e.g., a glass slide), and the section is allowed to "melt" on the substrate. Those skilled in the art will recognize other immobilization techniques that can be used as well.

The invention may involve the ejection of fluids of virtually any type and amount desired. The fluids may be aqueous and/or nonaqueous. Examples of fluids include, but are not limited to, aqueous fluids (including water per se and water-solvated ionic and non-ionic solutions organic solvents, and lipidic liquids); suspensions of immiscible fluids; and suspensions or slurries of solids in liquids. Thus, the fluid may contain, for example, biomolecules such as peptides or nucleotides, enzymes, and/or cellular matter such as whole cells and cell extracts. Often, the fluid is selected to preferentially interact with selected moieties on the compositionally nonuniform sample surface. For example, if peptidic digestion is desired, then typsin, pepsin, and other well-known compounds for peptidic digestion may be included in the fluid. When the invention is used for sample analysis, the fluid may be an analysis-enhancing fluid. That is, the analysis-enhancing fluid may be employed to increase yield of useful information during surface analysis. In some instances, the analysis-enhancing fluid comprises an analysis-enhancing moiety and a carrier fluid. For example, the analysis-enhancing moiety may be a label moiety that is fluorescently, magnetically, or radioactively detectable. The carrier fluid in such cases may include, for example, combinations of water, acetonitrile, alcohols such as ethanol, and ketones such as acetone.

As discussed below, the invention is particularly suited formass spectrometry analysis applications involving laser-assisted ionization and desorption. MALDI and SELDI are two examples of such applications. When the invention is used in the context of mass spectrometry, the analysis-enhancing fluid comprises a mass-spectrometry matrix material. Any of a number of photoabsorbing matrix materials known in the art may be employed, and examples of matrix materials for sample analysis include, but are not limited to, 6-aza-2-thiothymine, caffeic acid, 2,5-dihydroxybenzoic acid, α-cyano-4-hydroxy cinnamic acid, 3-hydroxypicolinic acid, 2-pyrazinecarboxylic acid, and combinations thereof. A plurality of analysis-enhancing fluids may be applied to an analyte to optimize experimental parameters such as signal and reproducibility. Different subregions of a single sample could also be probed with a variety of matrices to enhance a particular component of interest. For example, 3-hydroxypicolinic acid is commonly used for the analysis of glycoproteins.

Although there is great flexibility in the construction of a suitable reservoir for the invention, some constructions are more suitable than others. As an initial matter, the material used in the construction of the reservoir should be compatible with the fluids contained therein. Thus, if it is intended that the reservoir contain an organic solvent such as acetonitrile, polymers that dissolve or swell in acetonitrile would be unsuitable for use in forming the reservoirs. For water-based fluids, a number of materials are suitable for the construction of the reservoir and include, but are not limited to, ceramics such as silicon oxide and aluminum oxide, metals such as stainless steel and platinum, and polymers such as polyester and polytetrafluoroethylene. The reservoir is preferably detachable from the inventive device, but this is not a necessity. When more than one reservoir is needed, a well plate may be used to contain fluids that are to be ejected. In such a case, the reservoirs, or wells, of the well plate are preferably substantially acoustically indistinguishable from one another. Also, unless it is intended that the ejector be submerged in the fluid to be ejected, the reservoirs or well plates must have acoustic transmission properties sufficient to allow acoustic radiation from the ejector to be conveyed to the surfaces of the fluids to be ejected. Typically, this involves providing reservoir, or well, bases that are sufficiently thin to allow acoustic radiation to travel therethrough without unacceptable dissipation.

Many well plates suitable for use with the employed device are commercially available and may contain, for example, 96, 384, 1536, and 3456 wells per well plate. Manufacturers of suitable well plates for use in the employed device include Corning, Inc. (Corning, N.Y.) and Greiner America, Inc. (Lake Mary, Fla.). The availability of such commercially available well plates, however, does not preclude the manufacture and use of custom-made well plates that contain at least about 10,000 wells, or as many as 100,000 wells or more. In some instances, the reservoirs may represent a portion of a microfluidic device, as discussed below. Microfluidic devices are available from ACLARA BioSciences, Inc. (Mountain View, Calif.), Caliper Technologies Corp. (Mountain View, Calif.), and Fluidigm Corp. (South San Francisco, Calif.). The combined employment of focused acoustic ejection and microfluidic devices are discussed in U.S. Ser. No. 10/066,546.

Because of the precision that is possible using the inventive technology, the device may be used to eject droplets from a reservoir adapted to contain no more than about 100 nanoliters of fluid, preferably no more than about 10 nanoliters of fluid. In certain cases, the ejector may be adapted to eject a droplet from a reservoir adapted to contain about 1 to about 100 nanoliters of fluid. This is particularly useful when the fluid to be ejected contains rare or expensive biomolecules, wherein it may be desirable to eject droplets having a volume of about 1 picoliter or less (i.e., in the range of about 0.025 pL to about 1 pL), which corresponds to deposited droplet diameters of about 20 $\mu$m or less.

In addition, the invention sometimes involves the repeated deposition of a plurality of droplets on the sample surface. In some instances, droplets are deposited on the sample surface at a single designated site. In other instances, droplets are deposited on the sample surface at different designated sites. In such a case, it is preferred that the different designated sites form an array. Focused acoustic ejection enables the preparation of arrays that may have nearly limitless densities of array elements (i.e., sites). In some instances, the density of the array elements is in the range of approximately 10 to approximately 250,000 array elements (i.e., sites) per square centimeter of sample, typically in the range of approximately 400 to approximately 100,000 array elements per square centimeter of sample surface. However, it must be emphasized that the present method enables preparation of far higher density arrays as well, i.e., arrays comprised of at least about 1,000,000 array elements per square centimeter of sample surface, or even in the range of about 1,500,000 to 4,000,000 elements per square centimeter of sample surface.

As alluded to above, a plurality of reservoirs may be provided, each containing a different fluid. In such a case, focused acoustic energy may be applied in a manner effective to eject a droplet of fluid from each reservoir such that the droplets from the reservoirs are deposited on the sample surface. The droplets of different fluids may be deposited at a single designated site or at different designated sites.

When an analysis-enhancing fluid is deposited on the sample surface, the sample is typically subjected to conditions effective to allow the analysis-enhancing fluid to interact with the sample surface, rendering the sample surface suitable for analysis. Depending on the type of analysis desired, any of a number of different types of interactions may take place between the analysis-enhancing fluid and the sample surface. Thus, for example, when the analysis-enhancing fluid comprises an analysis-enhancing moiety and a carrier fluid, the carrier fluid is evaporated from the sample surface, thereby leaving the analysis-enhancing moiety in a concentrated form on the sample surface. In some instances, the analysis-enhancing fluid is solidified on the sample surface. Furthermore, the analysis-enhancing fluid may be selected to break down or digest the constituents of the sample surface. As another example, the analysis-enhancing moiety may bind with selective moieties on the sample surface, thereby rendering the substrate surface suitable for analysis. Once appropriate interaction has taken place, the sample at the designated site may be analyzed.

Any of a number of analyses may be carried out for the sample at the designated site or sites. Surface-specific properties may be measured by surface-specific physical techniques and physical techniques that are adapted to surface characterization. Various physical surface characterization techniques include, without limitation, diffractive techniques, spectroscopic techniques, microscopic surface imaging techniques, surface ionization mass spectroscopic techniques, thermal desorption techniques, and ellipsometry. It should be appreciated that these classifications are arbitrarily made for purposes of explication, and some overlap may exist. Thus, for example, the inventive device may incorporate analyzing means such as microscopes, optical detectors, fluorescence detectors, magnetic detectors, radioactivity detectors, and combinations thereof.

One important use of the invention involves sample preparation for mass spectrometric techniques such as MALDI and SELDI. As discussed above, the accuracy and reliability of such mass spectrometric techniques require control over the formation of the sample matrix. Thus, to provide control of analyte ionization and desorption, it is preferred that the features be formed in a consistent manner. This typically requires the deposition of fluid droplets of substantially identical size on a substrate. For example, if the substrate already contains a matrix material, sample droplets containing the same concentration of analyte moieties and of a substantially identical size may be deposited as an array on the substrate. As another example, if the substrate already contains sample materials, identically sized droplets of one or more matrix materials may be deposited on selected sites to form features that facilitate sample ionization and desorption upon bombardment of laser photons. In either case, the matrix material enables the absorption of laser energy to volatilize and ionize the analyte, while preventing analyte decomposition by absorbing significant amounts of laser energy.

In short, either or both of the matrix materials and the analyte are deposited on the substrate surface consistently and homogeneously to the substrate surface from site to site. If either the matrix material or the analyte is absent, or is present in an inappropriate quantity at a feature, proper ionization will not take place, thereby resulting in inoperative or suboptimal MALDI performance. For example, when fluids are deposited manually to form features on a substrate or a sample surface, one can expect highly variable signal strengths from the different individual features. In many cases, no signal is detected. Moreover, manual deposition of fluid features does not typically enable the study of substructures in a sample wherein the sample features have a cross-sectional dimension of about 10–20 $\mu$m.

Acoustic ejection, as described above, allows highly reproducible quantities of MALDI matrix material, analyte, or another chemical entity to be deposited on regions of a substrate surface. As described in U.S. patent application Ser. No. 09/727,392, employment of acoustic ejection to dispense fluids results in consistency of feature shape, droplet directionality, and ejected volume that is unmatched by printing methods generally known in the art. Features containing matrix materials on the order of micrometers can be created. Due to the repeatability and precision in placement of droplets through acoustic ejection, additional matrix material may be added to any desired feature site. That is, for any feature site, matrix material may be incrementally deposited to ensure that the amount of matrix material at that feature site is optimized for data acquisition.

Furthermore, the invention is well suited for mass-spectrometric imaging. Such imaging has been described in detail in U.S. Pat. No. 5,808,300 to Caprioli and in Stoeckli et al. (2001), "Imaging Mass Spectrometry: A New Technology for the Analysis of Protein Expression in Mammalian Tissues," *Nature Medicine* 7(4):493–496. In essence, these references describe the use of MALDI mass spectrometry to generate images of samples according to one or more mass-to-charge ratios. That is, MALDI mass spectrometry is used to analyze the spatial arrangement of specific molecules within a tissue sample. The analysis involves first preparing a test specimen by coating a thin sample layer with an energy absorbant matrix. Then, the test specimen is probed with a laser beam such that a first designated laser spot on the test specimen releases sample molecules. The test specimen is then moved relative to the laser beam and struck with the laser beam such that subsequent designated laser spots on the test specimen release additional sample molecules. The atomic mass of the released sample molecules are measured and mapped to determine the spatial arrangement of specific molecules within the sample.

Thus, for mass spectrometric analysis using the invention, acoustic ejection is employed to coat either an entire sample surface or only designated sites thereon with a mass-spectrometry matrix material. Acoustic ejection provides control over the formation of the sample/matrix complex on the sample surface. For example, acoustic deposition techniques may correct for any potential deficiency in the presence of a required fluid by ejecting additional matrix material. Because acoustic ejection allows for precise placement of ejected droplets, the location of matrix materials at the designated sites will be known with a higher degree of confidence. As a result, there is no need for the laser to probe a sample multiple times simply to locate the complex. Increasing the frequency of successful experiments greatly reduces the time for sample analysis, leading to greater sample throughput.

In addition, designated sites may correspond to sample regions of specific analytes. If the droplets deposited at the same designated site contains different moieties, the concentration of the different moieties that form the complex can be controlled. Since different analysis-enhancing fluids may specifically enhance one type of analyte over another, the experimenter could effectively analyze an impure sample. For example, if a mixture of nucleic acid and protein were deposited on a substrate, one could preferentially acquire a nucleic acid signal by the deposition of 2-amino-5-nitropyridine on the analyte, and then acquire a protein signal via the deposition of 6-aza-2-thiothymine. One could deposit the two analysis-enhancing fluids on two separate subregions of a single analyte region of a sample, or on two or more regions of the same analyte. A region is an area containing analyte that is not contiguous with an adjacent region. A subregion is an area of analyte within a non-contiguous region.

Sufficient energy is applied to the sites to ionize and release the sample molecules from the sample surface for analysis. This may involve bombarding one or more designated sites with photons through the use of an optional laser. As discussed above, different regions of a single sample may be co-crystallized or complexed with a variety of matrices to facilitate the ionization of a particular component of interest. The energy may be applied, for example, by bombarding the sites with photons (e.g., through use of a laser), electrons, and/or ions. Ionization and release of sample molecules may be enhanced through heating, directing focused acoustic energy to, and/or passing an electrical current through, at least one site. Once released, the ions may be directed to a mass analyzer/detector. By collecting such mass spectrometric data for a plurality of sites, a compositional map of the sample surface can be constructed.

Figure 1:
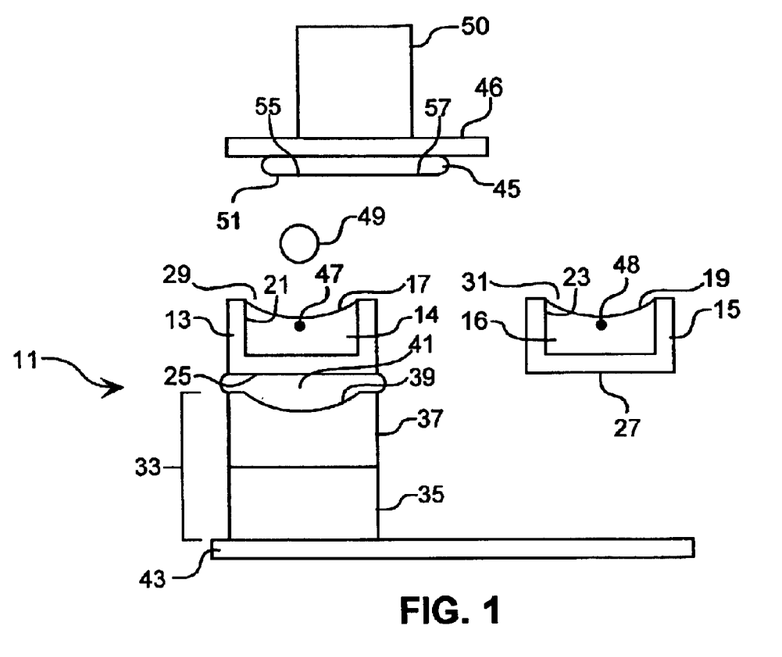
FIG. 1 schematically illustrates the deposition of a first analysis-enhancing fluid on a surface of the tissue sample at a first site.
Figure 2:
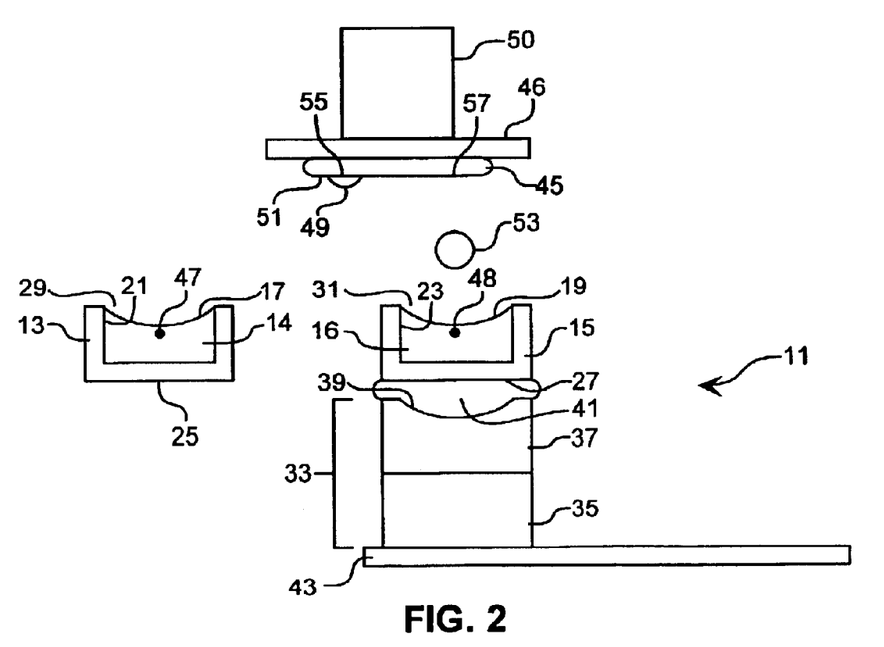
FIG. 2 schematically illustrates the deposition of a second analysis-enhancing fluid on a surface of the tissue sample at a second site.

FIG. 1 illustrates an embodiment of the inventive method for analyzing a cellular sample through mass spectrometry. As with all figures referenced herein, in which like parts are referenced by like numerals, FIG. 1 is not to scale, and certain dimensions may be exaggerated for clarity of presentation. A device for acoustically depositing a fluid on a surface of a cellular sample is depicted in FIGS. 1 and 2. This device is similar in construction to the acoustic ejection device described in U.S. patent application Ser. Nos. 09/964, 212 and 09/669,996. The device 11 includes a plurality of reservoirs, i.e., at least two reservoirs, although only one reservoir may be required in some instances. A first reservoir is indicated at 13, and a second reservoir is indicated at 15. Each is adapted to contain a fluid having a fluid surface, e.g., a first fluid 14 and a second fluid 16 having fluid surfaces respectively indicated at 17 and 19. Typically, fluids 14 and 16 are different. In order to prepare the sample surface for mass spectrometric analysis, fluids 14 and 16 each comprise a mass-spectrometry matrix material.

The reservoirs are shown in their preferred construction and are substantially identical and acoustically indistinguishable. However, identical construction is not a requirement. In addition, the reservoirs are shown as separate removable components, but they may, if desired, be fixed within a plate or other substrate. For example, the plurality of reservoirs may comprise individual wells in a well plate, optimally although not necessarily, arranged in an array. Each of the reservoirs 13 and 15 is preferably axially symmetric as shown, having vertical walls 21 and 23 extending upward from circular reservoir bases 25 and 27, and terminating at openings 29 and 31, respectively, although other reservoir shapes may be used. The material and thickness of each reservoir base should be such that acoustic radiation may be transmitted therethrough and into the fluid contained within the reservoirs.

The device also includes an acoustic ejector 33, comprised of an acoustic radiation generator 35 for generating acoustic radiation and a focusing means 37 for focusing the acoustic radiation at a focal point within the fluid from which a droplet is to be ejected near the fluid surface. As shown in FIGS. 1 and 2, the focusing means 37 may comprise a single solid piece having a concave surface 39 for focusing acoustic radiation, but the focusing means may be constructed in other ways as discussed below. The acoustic ejector 33 is thus adapted to generate and focus acoustic radiation so as to eject a droplet of fluid from each of the fluid surfaces 17 and 19 when acoustically coupled to reservoirs 13 and 15, and thus to fluids 14 and 16, respectively. The acoustic radiation generator 35 and the focusing means 37 may function as a single unit controlled by a single controller, or they may be independently controlled, depending on the desired performance of the device. Typically, single ejector designs are preferred over multiple ejector designs because accuracy of droplet placement and consistency in droplet size and velocity are more easily achieved with a single ejector. However, the invention is not limited to single ejector designs.

For the present invention, any of a variety of focusing means that include curved surfaces or Fresnel lenses known in the art may be employed in conjunction with the present invention. Such focusing means are described in U.S. Pat. Nos. 4,308,547 to Lovelady et al. and 5,041,849 to Quate et al., as well in as U.S. Ser. Nos. 09/964,212 and 09/669,996. In addition, there are a number of ways to acoustically couple the ejector to each individual reservoir and thus to the fluid therein. Although acoustic coupling can be achieved through direct contact with the fluid contained in the reservoirs, the preferred approach is to acoustically couple the ejector to the reservoirs and reservoir fluids without allowing any portion of the ejector (e.g., the focusing means) to contact any of the fluids to be ejected. To this end, the present invention provides an ejector positioning means for positioning the ejector in controlled and repeatable acoustic coupling with each of the fluids in the reservoirs to eject droplets therefrom without submerging the ejector therein.

To avoid ejector submersion, direct or indirect contact is typically established between the ejector and the external surface of each reservoir. When direct contact is used in order to acoustically couple the ejector to each reservoir, it is preferred that the direct contact be wholly conformal to ensure efficient acoustic energy transfer. That is, the ejector and the reservoir should have corresponding surfaces adapted for mating contact. Thus, if acoustic coupling is achieved between the ejector and reservoir through the focusing means, it is desirable for the reservoir to have an outside surface that corresponds to the surface profile of the focusing means. Without conformal contact, efficiency and accuracy of acoustic energy transfer may be compromised. In addition, since many focusing means have a curved surface, the direct contact approach may necessitate the use of reservoirs that have a specially formed inverse surface.

Optimally, acoustic coupling is achieved between the ejector and each of the reservoirs through indirect contact, as illustrated in FIGS. 1 and 2. In the figures, an acoustic coupling medium 41 is placed between the ejector 33 and the base 25 of reservoir 13, with the ejector and reservoir located at a predetermined distance from each other. The acoustic coupling medium may be an acoustic coupling fluid, preferably an acoustically homogeneous material in conformal contact with both the acoustic focusing means 37 and each reservoir. In addition, it is important to ensure that the fluid medium is substantially free of material having different acoustic properties than the fluid medium itself. As shown, the first reservoir 13 is acoustically coupled to the acoustic focusing means 37 such that an acoustic wave generated by the acoustic radiation generator is directed by the focusing means 37 into the acoustic coupling medium 41, which then transmits the acoustic radiation into the reservoir 13.

In operation, reservoirs 13 and 15 of the device are each filled with first and second fluids 14 and 16, respectively, as shown in FIG. 1. The acoustic ejector 33 is positionable by means of ejector positioning means 43, shown below reservoir 13, in order to achieve acoustic coupling between the ejector and the reservoir through acoustic coupling medium 41. Cellular sample 45 in the form of a tissue section is placed on a substrate 46, which is positioned above and in proximity to the first reservoir 13 such that one surface of the tissue, shown in FIG. 1 as the underside surface 51, faces the reservoir and is substantially parallel to the surface 17 of the fluid 14 therein. Once the ejector, the reservoir, and the tissue sample 45 are in proper alignment, the acoustic radiation generator 35 is activated to produce acoustic radiation that is directed by the focusing means 37 to a focal point 47 near the fluid surface 17 of the first reservoir. As a result, droplet 49 is ejected from the fluid surface 17 onto a designated site 55 on the underside surface 51 of the tissue sample. The ejected droplet may be retained on the tissue surface through adsorption and/or other surface effects. In some instances, the droplet may be solidified on the tissue surface after contact; in such an embodiment, it may be necessary to maintain the tissue at a low temperature, i.e., a temperature that results in droplet solidification after contact.

Then, as shown in FIG. 2, a sample positioning means 50 repositions the cellular sample 45 on the substrate 46 over reservoir 15 in order to receive a droplet therefrom at a second designated site 57. FIG. 2 also shows that the ejector 33 has been repositioned by the ejector positioning means 43 below reservoir 15 and in acoustically coupled relationship thereto by virtue of acoustic coupling medium 41. Once properly aligned as shown in FIG. 2, the acoustic radiation generator 35 of ejector 33 is activated to produce acoustic radiation that is then directed by focusing means 37 to a focal point 48 within fluid 16 near the fluid surface 19, thereby ejecting droplet 53 onto the cellular sample at the second designated site 57. It should be evident that such operation is illustrative of how the inventive device may be used to eject a plurality of fluids from reservoirs in order to form a pattern, e.g., an array, on the cellular sample surface 51. It should be similarly evident that the device may be adapted to eject a plurality of droplets from one or more reservoirs onto the same site of the cellular sample surface.

It will be appreciated that various components of the device may require individual control or synchronization to form an array on a sample surface. For example, the ejector positioning means may be adapted to eject droplets from each reservoir in a predetermined sequence associated with an array to be prepared on a sample surface. Similarly, the sample positioning means for positioning the sample with respect to the ejector may be adapted to position the sample surface to receive droplets in a pattern or array thereon. Either or both positioning means, i.e., the ejector positioning means and the sample positioning means, may be constructed from, for example, motors, levers, pulleys, gears, a combination thereof, or other electromechanical or mechanical means known to one of ordinary skill in the art. It is preferable to ensure that there is a correspondence between sample movement, ejector movement, and ejector activation to ensure proper array formation.

Figure 3:
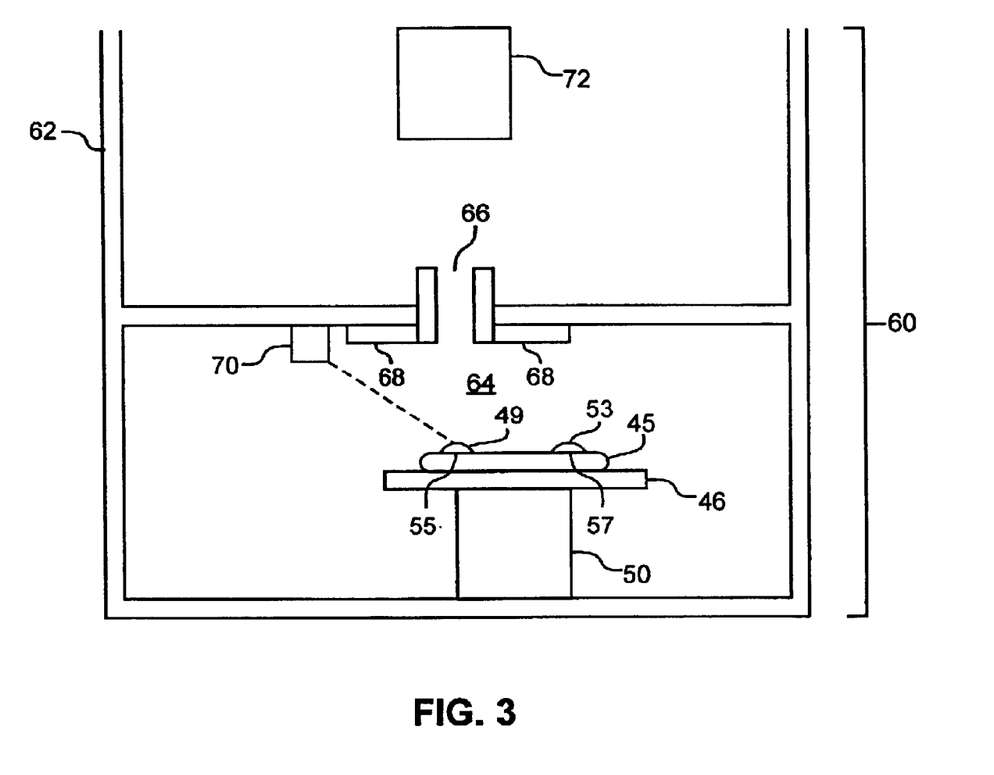
FIG. 3 schematically illustrates the ionization of the sample at the tissue surface sites.

FIG. 3 schematically illustrates an ionization chamber of a mass spectrometer. The ionization chamber 60 comprises a housing 62 containing an ionization region 64, and an interface comprising a capillary 66 and an electrode 68 for attracting ions toward the capillary 66. An energy applying means 70 in the form of a laser and a sample positioning means 50 are provided as well. In operation, the substrate 46 is immobilized with respect to the positioning means 50. As shown, the tissue sample 45 has been subjected to conditions effective to allow the analysis-enhancing fluid droplets 49 and 53 to interact with sample surface 51 so as to render the sample surface suitable for analysis at the designated sites 55 and 57, respectively. The electrode 68 is charged, and once the first designated site 55 and the capillary 66 are in proper alignment, the laser 70 is activated. As a result, ionized sample molecules, formed at the first designated site 55, are released into ionization region 64. The ions are then drawn toward the electrode 68, enter the capillary 66, and are subsequently analyzed by mass analyzer/detector 72. Examples of such mass analyzers/detectors include multipole detectors, e.g., quadruple detectors, which employ a charged surface that attracts or repels the ionized sample molecule. The identical procedure may be carried out for ionizing sample molecules at the second designated site 57. Additional charged surfaces (not shown) may be placed in the ionization chamber to direct the trajectory of ions.

Thus, it should be evident that the acoustic ejection device illustrated in FIGS. 1 and 2 may share a common registration system with the mass spectrometer illustrated in FIG. 3. This ensures that the sample positioning means for the acoustic ejection device and the mass spectrometer can carry out the identical sample movement system. In turn, laser irradiation will occur at precisely the designated sites. It should be further evident that these procedures may be controlled using commercially available and/or customized software.

The embodiment illustrated in the figures provides a number of previously unrealized advantages in the art of mass spectrometry imaging. For example, the invention may be used in the analysis and imaging of peptides and proteins in tumors and other abnormal tissue. With the accuracy and precision associated with acoustic droplet deposition, the analysis may quantify or compare the levels of specific proteins that are more highly expressed in tumors with those that greatly diminished in expression, relative to normal tissue. Without using acoustic deposition of mass spectrometry matrix materials, accurate location and quantitation of the proteins may not be possible. Furthermore, the invention great improves mass spectrometric imaging that may provide a greater understanding of other types of protein expression, e.g., associated with Parkinson's disease, as well drugs and metabolites in tissue.

Furthermore, acoustic deposition increases the spatial resolutions of MALDI imaging because the diameter of the fluid droplets deposited can be controlled to approach the diameter of the laser beam used to scan the sample. This diameter is typically about 2 to about 25 $\mu$m. This is important because analysis-enhancing fluids may liberate sample molecules from the sample surface to be analyzed. If droplets exceeding the diameter of the laser focal spot are used, liberated components molecules from different regions of a tissue sample may "mix" and result in cross-contamination. This mixing creates inaccurate or false mass spectrometric images that do not reflect the actual composition of the sample surface.

Thus, variations of the present invention will be apparent to those of ordinary skill in the art. In addition, it is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

We claim:

1. A method for acoustically depositing a fluid on a contiguous surface of a cellular sample comprising:
    (a) providing a reservoir containing a fluid;
    (b) positioning the cellular sample such that at least one designated site on the contiguous surface is located in droplet-receiving relationship to the reservoir; and
    (c) applying focused acoustic energy in a manner effective to eject a droplet of the fluid from the reservoir such that the droplet is deposited on the at least one designated site.

2. The method of claim 1, wherein the cellular sample comprises cells from a cellular culture.

3. The method of claim 1, wherein the cellular sample is a tissue.

4. The method of claim 3, wherein the tissue is an animal tissue.

5. The method of claim 4, wherein the animal tissue is mammalian tissue.

6. The method of claim 1, wherein surface of the cellular sample is compositionally nonuniform.

7. The method of claim 1, wherein the fluid is an analysis-enhancing fluid.

8. The method of claim 1, wherein the analysis-enhancing fluid comprises a detectable label moiety.

9. The method of claim 8, wherein the label moiety is a fluorescent moiety.

10. The method of claim 8, wherein the label moiety is a magnetic moiety.

11. The method of claim 8, wherein the label moiety is a radioactive moiety.

12. The method of claim 1, wherein the fluid contains a biomolecule.

13. The method of claim 12, wherein the biomolecule is peptidic.

14. The method of claim 12, wherein the biomolecule is nucleotidic.

15. The method of claim 12, wherein the biomolecule is enzymatic.

16. The method of claim 1, wherein the fluid contains cellular matter.

17. The method of claim 16, wherein the cellular matter comprises at least one whole cell.

18. The method of claim 16, wherein the cellular matter comprises at least one cell extract.

19. The method of claim 6, wherein the fluid is selected to preferentially interact with selected moieties on the compositionally nonuniform sample surface.

20. The method of claim 7, further comprising, after step (c), (d) subjecting the sample to conditions effective to allow the analysis-enhancing fluid to interact with the sample surface so as to render the sample surface suitable for analysis.

21. The method of claim 20, wherein the analysis-enhancing fluid comprises an analysis-enhancing moiety and a carrier fluid.

22. The method of claim 21, wherein the carrier fluid is evaporated from the sample surface in step (d).

23. The method of claim 20, wherein the analysis-enhancing fluid is solidified on the sample surface in step (d).

24. The method of claim 23, wherein the analysis-enhancing fluid comprises a mass-spectrometry matrix material.

25. The method of claim 24, wherein the mass-spectrometry matrix material is a photoabsorbing matrix material.

26. The method of claim 20, further comprising, after step (d), (e) analyzing the sample at the at least one designated site.

27. The method of claim 26, further comprising, after step (d) and before step (e), (d') applying effective energy to the at least one designated site to release sample molecules from the sample surface for analysis.

28. The method of claim 27, wherein the energy applied in step (d') is effective to ionize the sample molecules released from the sample surface.

29. The method of claim 28, wherein step (d') comprises bombarding the at least one designated site with photons.

30. The method of claim 29, wherein photonic bombardment is carried out using a laser.

31. The method of claim 26, wherein step (e) comprises determining the molecular weight of the sample molecules.

32. The method of claim 26, wherein step (e) comprises determining the extent of any interaction between the analysis-enhancing fluid and the sample surface.

33. The method of claim 1, wherein step (c) is repeated to deposit a plurality of droplets on the sample surface.

34. The method of claim 33, wherein the droplets are deposited on the sample surface at a single designated site.

35. The method of claim 33, wherein the droplets are deposited on the sample surface at different designated sites.

36. The method of claim 35, wherein the different designated sites form an array.

37. The method of claim 36, further comprising, after step (c), (d) subjecting the sample to conditions effective to allow the fluid to interact with the sample surface at the different designated sites so as to render the sample surface suitable for analysis.

38. The method of claim 37, further comprising, after step (d), (e) analyzing the composition of the sample at each designated site.

39. The method of claim 38, further comprising, during or after step (e), (f) preparing a compositional map of the cellular sample surface using the analysis of step (e).

40. The method of claim 1, wherein step (a) comprises providing a plurality of reservoirs, each containing a different analysis-enhancing fluid; and step (c) comprises applying focused acoustic energy in a manner effective to eject a droplet of fluid from each reservoir such that the droplets from the reservoirs are deposited on at least one designated site on the sample surface.

41. The method of claim 40, wherein droplets of different analysis-enhancing fluids are deposited on the sample surface at a single designated site.

42. The method of claim 41, wherein the droplets are deposited on the sample surface at different designated sites.

43. The method of claim 42, further comprising, after step (c), (d) subjecting the sample to conditions effective to allow the fluid to interact with the sample surface at the different designated sites so as to render the sample surface suitable for analysis.

44. The method of claim 43, further comprising, after step (d), (e) analyzing the sample at each designated site.

45. The method of claim 44, wherein the different designated sites form an array.

46. The method of claim 45, further comprising, during or after step (e), (f) preparing a compositional map of the cellular sample surface using the analysis of step (e).

47. A system for acoustically depositing a fluid on a contiguous surface of a cellular sample comprising:
a reservoir containing a fluid;
an acoustic ejector comprising an acoustic radiation generator for generating acoustic radiation and a focusing means for focusing the acoustic radiation generated;
an acoustic ejector positioning means for positioning the acoustic ejector in acoustic coupling relationship to the reservoir;
a cellular sample having a contiguous surface; and
a sample positioning means for positioning the cellular sample such that at least one designated site on the contiguous surface is in droplet-receiving relationship to the reservoir.

48. The system of claim 47, wherein the fluid is an analysis-enhancing fluid.

49. The system of claim 48, wherein the analysis-enhancing fluid comprises a mass-spectrometry matrix material.

50. The system of claim 49, wherein the mass-spectrometry matrix material is a photoabsorbing matrix material.

51. The system of claim 48, wherein the analysis-enhancing fluid is selected to interact preferentially with selected moieties on the sample surface.

52. The system of claim 48, wherein the analysis-enhancing fluid comprises a detectable label moiety.

53. The system of claim 47, further comprising an analyzing means for analyzing the composition of the sample at a designated site.

54. The system of claim 53, wherein the analyzing means comprises a mass spectrometer.

55. The system of claim 53, wherein the analyzing means comprises a detector selected from the group consisting of optical detectors, radiation detectors, and magnetic detectors.

56. The system of claim 53, further comprising an energy applying means for applying energy to the at least one designated site to effect release and ionization of sample molecules from the sample surface for analysis.

57. The system of claim 56, wherein the energy applying means comprises a photon bombarding means for bombarding the at least one designated site with photons.

58. The system of claim 57, wherein the photon bombarding means comprises a laser.

59. The system of claim 47, wherein the sample positioning means is adapted to controllably position the sample such that a plurality of designated sites on the cellular sample surface are successively placed in droplet receiving relationship to the reservoir.

60. The system of claim 59, wherein the designated sites form an array.

61. The system of claim 47, wherein the cellular sample surface is substantially planar.

62. The system of claim 47, further comprising at least one additional reservoir. wherein each reservoir contains a different fluid.

63. The system of claim 62, comprising a single ejector, wherein the acoustic ejector positioning means is adapted to position the acoustic ejector in acoustic coupling relationship to each of the reservoirs.

64. A method for analyzing a contiguous surface of a cellular sample, comprising:
(a) providing a reservoir containing an analysis-enhancing fluid;
(b) positioning the cellular sample such that a designated site on the contiguous sample surface is in droplet-receiving relationship to the fluid containing reservoir, wherein the designated site is one of a plurality of designated sites within an array of such sites;
(c) applying focused acoustic energy in a manner effective to elect a droplet of the fluid from the reservoir such that the droplet is deposited on the designated site;
(d) repeating steps (b) and (c) with each different designated site so that at least one droplet is deposited at each designated site;
(e) applying energy to each of the designated sites to effect release of sample molecules therefrom; and
(f) analyzing the released sample molecules.

65. The method of claim 64, wherein step (f) comprises performing mass spectrometric analysis on the sample molecules.

66. The method of claim 65, further comprising during or after step (f), producing a compositional map of the cellular sample surface from the results of the mass spectrometric analysis.

67. A system for acoustically depositing a fluid on a contiguous surface of a cellular sample, comprising:
a reservoir containing an analyte-enhancing fluid;
an acoustic ejector comprising an acoustic radiation generator for generating acoustic radiation and a focusing means for focusing the acoustic radiation generated;
an acoustic ejector positioning means for positioning the acoustic ejector in acoustic coupling relationship to the reservoir;
a cellular sample having a contiguous surface;
a sample positioning means for positioning a cellular sample such that a plurality of different designated sites within an array of such sites on the contiguous cellular sample surface are successively placed in droplet-receiving relationship to the reservoir;
an energy applying means for applying energy to the designated sites to effect release and ionization of sample molecules therefrom; and
an analyzing means for analyzing the sample molecules from the designated sites.

68. The system of claim 67, wherein the energy applying means comprises a photon bombarding means for bombarding the designated site with photons.

69. The system of claim 68, wherein the photon bombarding means comprises a laser.

70. The system of claim 69, wherein the analyzing means comprises a mass spectrometer.

* * * * *